United States Patent
Asao

(10) Patent No.: US 8,991,261 B2
(45) Date of Patent: Mar. 31, 2015

(54) ACOUSTIC WAVE MEASURING APPARATUS, ACOUSTIC WAVE IMAGING APPARATUS AND METHOD FOR CONTROLLING ACOUSTIC WAVE MEASURING APPARATUS

(75) Inventor: Yasufumi Asao, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 307 days.

(21) Appl. No.: 13/394,664

(22) Filed: Mar. 7, 2012

(65) Prior Publication Data
US 2012/0167693 A1   Jul. 5, 2012

(30) Foreign Application Priority Data
Oct. 19, 2009   (JP) .................... 2009-240299

(51) Int. Cl.
G01H 9/00 (2006.01)
G01N 21/17 (2006.01)
A61B 5/00 (2006.01)
G01N 29/24 (2006.01)

(52) U.S. Cl.
CPC .......... *G01N 21/1702* (2013.01); *A61B 5/0059* (2013.01); *A61B 5/0097* (2013.01); *G01N 29/2418* (2013.01); *G01N 2021/1706* (2013.01)
USPC .......................................................... 73/655

(58) Field of Classification Search
USPC .................................. 73/587, 632, 641, 655
See application file for complete search history.

(56) References Cited

U.S. PATENT DOCUMENTS

| | | | | |
|---|---|---|---|---|
| 5,348,002 A * | 9/1994 | Caro | ............................... | 600/310 |
| 5,713,356 A * | 2/1998 | Kruger | ............................ | 600/407 |
| 5,787,049 A * | 7/1998 | Bates | ................................ | 367/7 |
| 6,404,553 B1 * | 6/2002 | Wootton et al. | ................ | 359/573 |
| 6,999,174 B2 * | 2/2006 | Amonette et al. | ............. | 356/432 |
| 7,864,307 B2 * | 1/2011 | Fukutani et al. | ................. | 356/73 |
| 8,144,327 B2 * | 3/2012 | Nakajima et al. | .............. | 356/432 |

(Continued)

FOREIGN PATENT DOCUMENTS

| | | |
|---|---|---|
| JP | H11-099127 | 4/1999 |
| JP | 2004-008412 | 1/2004 |

(Continued)

OTHER PUBLICATIONS

A. Zegadi et al., "A Photoacoustic Spectrometer for Measuring Subgap Absorption Spectra of Semiconductors", *Rev. Sci. Instrum.*, vol. 65, No. 7, pp. 2238-2243 (Jul. 1994), XP000458536.

(Continued)

*Primary Examiner* — J M Saint Surin
(74) *Attorney, Agent, or Firm* — Fitzpatrick, Cella, Harper & Scinto

(57) ABSTRACT

An acoustic wave measuring apparatus includes a light source for radiating a light having a wavelength component in wavelength areas, light filters arranged in a light path from the light source to a subject and each to shut off or transmit the light in one of the wavelength areas, a detector for detecting an acoustic wave generated by the radiation, a controller for generating conditions having different combinations of the wavelength components contained in the light, and a signal processor for calculating an optical absorption coefficient of the subject for the light in each wavelength area based on a pressure of the acoustic wave detected under each of the conditions and a strength of the radiated light for each wavelength area under conditions.

15 Claims, 8 Drawing Sheets

(56) References Cited

U.S. PATENT DOCUMENTS

| | | | |
|---|---|---|---|
| 8,654,613 B2* | 2/2014 | Fukutani | 367/140 |
| 2003/0043880 A1* | 3/2003 | Meyler et al. | 374/32 |
| 2003/0229270 A1 | 12/2003 | Suzuki et al. | 600/178 |
| 2005/0228231 A1* | 10/2005 | MacKinnon et al. | 600/180 |
| 2008/0306371 A1* | 12/2008 | Fukutani et al. | 600/407 |
| 2009/0002685 A1* | 1/2009 | Fukutani et al. | 356/72 |
| 2010/0049049 A1* | 2/2010 | Asao et al. | 600/443 |
| 2010/0087733 A1* | 4/2010 | Nakajima et al. | 600/437 |

FOREIGN PATENT DOCUMENTS

| | | |
|---|---|---|
| JP | 2006-025802 | 2/2006 |
| JP | 2007-307007 | 11/2007 |
| JP | 2008-307372 | 12/2008 |
| JP | 2009-168597 | 7/2009 |

OTHER PUBLICATIONS

T. Autrey et al., "Tunable Ultraviolet Visible Photoacoustic Detection Analysis of the Sensitivity and Selectivity Provided by a Xenon Flash Lamp", *Anal. Chim. Acta*, vol. 434, pp. 217-222 (2001), XP007916771.

Office Action issued on Sep. 30, 2014, in counterpart Japanese Patent Application 2009-240299, with partial translation.

* cited by examiner

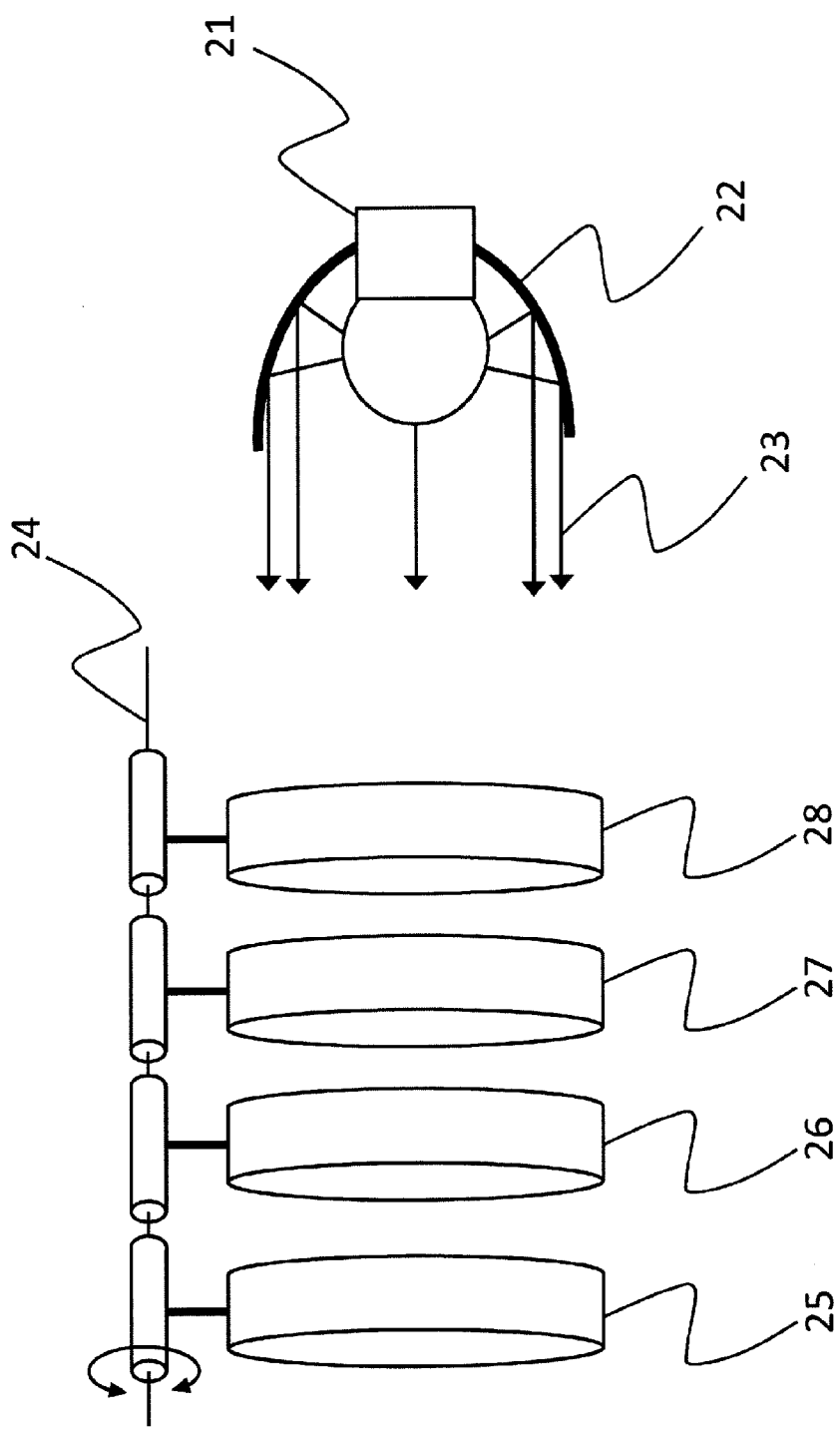

| B1 | B2 | B1 | B2 | B1 | B2 | B1 | B2 | B1 | B2 | B1 | B2 |
|----|----|----|----|----|----|----|----|----|----|----|----|
| B3 | B4 | B3 | B4 | B3 | B4 | B3 | B4 | B3 | B4 | B3 | B4 |
| B1 | B2 | B1 | B2 | B1 | B2 | B1 | B2 | B1 | B2 | B1 | B2 |
| B3 | B4 | B3 | B4 | B3 | B4 | B3 | B4 | B3 | B4 | B3 | B4 |
| B1 | B2 | B1 | B2 | B1 | B2 | B1 | B2 | B1 | B2 | B1 | B2 |
| B3 | B4 | B3 | B4 | B3 | B4 | B3 | B4 | B3 | B4 | B3 | B4 |
| B1 | B2 | B1 | B2 | B1 | B2 | B1 | B2 | B1 | B2 | B1 | B2 |
| B3 | B4 | B3 | B4 | B3 | B4 | B3 | B4 | B3 | B4 | B3 | B4 |
| B1 | B2 | B1 | B2 | B1 | B2 | B1 | B2 | B1 | B2 | B1 | B2 |
| B3 | B4 | B3 | B4 | B3 | B4 | B3 | B4 | B3 | B4 | B3 | B4 |
| B1 | B2 | B1 | B2 | B1 | B2 | B1 | B2 | B1 | B2 | B1 | B2 |
| B3 | B4 | B3 | B4 | B3 | B4 | B3 | B4 | B3 | B4 | B3 | B4 |

※ B1 TO B4 INDICATE BANDPASS FILTERS WHICH TRANSMITS ONLY THE LIGHT IN THE WAVELENGTH AREA INCLUDING WAVELENGTH PEAKS $\lambda 1$ TO $\lambda 4$, RESPECTIVELY.

FIG. 5

ACOUSTIC WAVE MEASURING APPARATUS, ACOUSTIC WAVE IMAGING APPARATUS AND METHOD FOR CONTROLLING ACOUSTIC WAVE MEASURING APPARATUS

TECHNICAL FIELD

The present invention relates to an acoustic wave measuring apparatus, an acoustic wave imaging apparatus and a method for controlling the acoustic wave measuring apparatus.

BACKGROUND ART

Generally, the imaging apparatuses using X rays, ultrasonic waves and MRI (magnetic resonance imaging) find wide application in the medical field. Also, in the medical field, the vigorous research effort is promoted on the optical imaging apparatus in which the light radiated on a living organism from a light source of a laser, etc. is propagated through a subject such as an organism, and by detecting this propagated light, the information inside the organism is obtained. An example of this optical imaging technique is photoacoustic tomography (PAT).

The PAT is a technique for visualizing the information related to the optical characteristic values inside a subject (See PTL 1: U.S. Pat. No. 5,713,356). Specifically, upon radiation of the pulse light on a subject from a light source, a photoacoustic signal (also called an acoustic wave, or typically, an ultrasonic wave) is generated, propagated and diffused from the tissue of the organism that has absorbed the optical energy. The temporal change in the acoustic wave is detected at a plurality of points surrounding the organism, and the signal thus obtained is analyzed. In this way, the optical characteristic values such as the initial pressure generation distribution caused by the light radiation in the subject and the optical energy absorption density distribution can be obtained.

The absorption spectra of oxidized hemoglobin and reduced hemoglobin in the blood, for example, show that the absorption amount changes at the wavelength of about 800 nm. By radiating the light in the wavelength of about 800 nm for measurement, therefore, the oxygen saturation degree of the blood can be determined. As a result, the point of a malignant tumor accompanied by the proliferation of new blood vessels, for example, can be specified. In the case where the distribution of the optical characteristic value of the tissue of an organism is determined in the comparative neighborhood of the surface of the organism, however, a wider wavelength range of, say, 400 nm to 1600 nm can be also used. In the case where the subject is not an organism, on the other hand, the wavelength range is not limited to the figures described above in an actual application.

It is generally known that an acoustic wave of a stronger sound pressure can be obtained by a shorter pulse width of the radiated light for an improved SN ratio. The pulse laser is often used, therefore, in the research on the photoacoustics, or especially, an application to an organism large in light attenuation. More specifically, the Q-switch YAG laser (wavelength of 1064 nm) is widely used which can easily produce a large output of several hundreds mJ or more with a pulse width of 10 ns or less.

The OPO (optical parametric oscillator) and the titanium sapphire (TiS) laser also are used which generate laser beams of various wavelengths with the second harmonic (wavelength of 532 nm) of the Q-switch YAG laser as an excitation source. By use of these lasers, the wavelength dependency of the optical absorption coefficient in the photoacoustic effect can be experimentally determined. An application of this fact to an organism can determine the oxygen saturation degree in the blood. In other words, it is well known that the wavelength dependency of the light absorption amount varies depending on how hemoglobin and oxygen are connected with each other, and by utilizing this phenomenon, a difference between the artery and the vein and a blood vessel newly generated by a tumor can be imaged.

(PTL 1) U.S. Pat. No. 5,713,356

SUMMARY OF INVENTION

The actual use of these lasers, however, poses issues described below.

A first problem is the one of manufacture. In order to secure a high SN ratio in the application of PAT to an organism, both a short pulse width and a high output are required to be achieved, and for this purpose, solid laser such as a Q-switch YAG laser is widely used. This requires the highly accurate alignment of members to oscillate the laser on the one hand, and an optical stool and a strong housing to suppress the characteristic variation with the vibration of the optical system on the other hand. For this reason, the apparatus size and weight cannot be reduced easily, and the apparatus cost is increased.

Especially, in the measuring operation with variable wavelengths, a variable wavelength laser is required to be introduced. In this case, as described above, various wavelengths are output using OPO or TiS with the second harmonic as an excitation source. Generally, however, the generation of the second harmonic from the fundamental wave produces a loss, and so does the generation of a laser light with a variable wavelength from the second harmonic. To obtain the desired output, therefore, a very large output of the fundamental wave is required, which leads to an increased apparatus cost.

A second problem is a requirement to introduce an equipment to secure the safety of the laser. The laser light has so high a linearity and a coherency that when the laser light erroneously enters an eye, for example, it may focus on the retina and reduce the visual acuity. The maximum permissible exposure (MPE) has, therefore, been laid down by the International Standards Commission as a safety standard of the laser light amount that can be radiated on the human body. Different MPE standards are set for the eye and the skin, and an application of PAT to the organism is designed so that a greater amount of optical energy can be radiated to diagnose a deeper organ within the MPE range for the skin. In the process, realization of a sufficient diagnosis depth requires a laser having a large light amount such as the laser class 4 having the highest order of strength. Various safety guidelines are laid down for use of class 4 laser. In order to prevent a person not wearing a protective goggle from approaching an apparatus and observing indirect light, for example, the installation of a specially shielded examination room is essential. Also, this dedicated examination room against the class 4 laser is required to comply with various rules. For example, a screen is required to be installed to prevent multiple reflection of the light diffused from the laser and workers are required to wear a cloth of a flameproof material. These factors restrict the introduction of the apparatus.

On the other hand, U.S. Pat. No. 5,713,356 (PTL 1) describes that a xenon flash lamp may be used in place of a laser. The xenon flash lamp, however, has a multiplicity of bright-line spectra (wavelength peaks). Also, the acoustic wave generated by the photoacoustic effect has the wavelength dependency, and therefore, the sound pressure is sometimes varied with the wavelength peak of the spectrum. As a result, when a light source has a plurality of peaks, a measurement value is difficult to analyze, thereby making it difficult to evaluate the oxygen saturation degree accurately.

The present invention has been achieved in view of these problems, and an object thereof is to provide a technique for conducting a measurement operation on an inexpensive acoustic wave measuring apparatus with a sufficient signal strength.

An acoustic wave measuring apparatus according to this invention comprising:

a light source that radiates a light having a wavelength component in a plurality of wavelength areas;

a plurality of light filters, arranged in a light path led from the light source to a subject, that shuts off or transmits the light in a specified one of the plurality of the wavelength areas respectively;

a detector that detects an acoustic wave generated upon light radiation on the subject;

a controller that changes a combination of the light filters and thus generates a plurality of light irradiating conditions having different combinations of the wavelength components contained in the light radiated on the subject; and a signal processor that calculates an optical absorption coefficient of the subject for the light in each wavelength area, based on a pressure of the acoustic wave detected under each of the plurality of the light irradiating conditions and a strength of the radiated light for each wavelength area under the plurality of the light irradiating conditions.

A method for controlling an acoustic wave measuring apparatus according to this invention, comprising the steps of:

generating a light having a wavelength component in a plurality of wavelength areas from a light source;

shutting off or transmitting the light using a plurality of light filters each for shutting off or transmitting the light in a specified one of the plurality of the wavelength areas on a light path led from the light source to a subject;

detecting an acoustic wave generated in the subject;

changing a combination of the light filters and thus generating a plurality of conditions having different combinations of the wavelength components contained in the light generated from the light source; and calculating an optical absorption coefficient of the subject for the light in each wavelength area, based on a pressure of the acoustic wave detected under each of the plurality of the conditions and a light strength for each wavelength area under each of the plurality of the conditions.

In the acoustic wave measuring apparatus according to the present invention, the measurement can be conducted with a sufficient signal strength while at the same time suppressing the apparatus cost.

Further features of the present invention will become apparent from the following description of exemplary embodiments with reference to the attached drawings.

BRIEF DESCRIPTION OF DRAWINGS

FIG. 3 is a diagram showing a light source according to a first embodiment.

FIG. 5 is a diagram showing a filter array according to a second embodiment.

Figure 1:
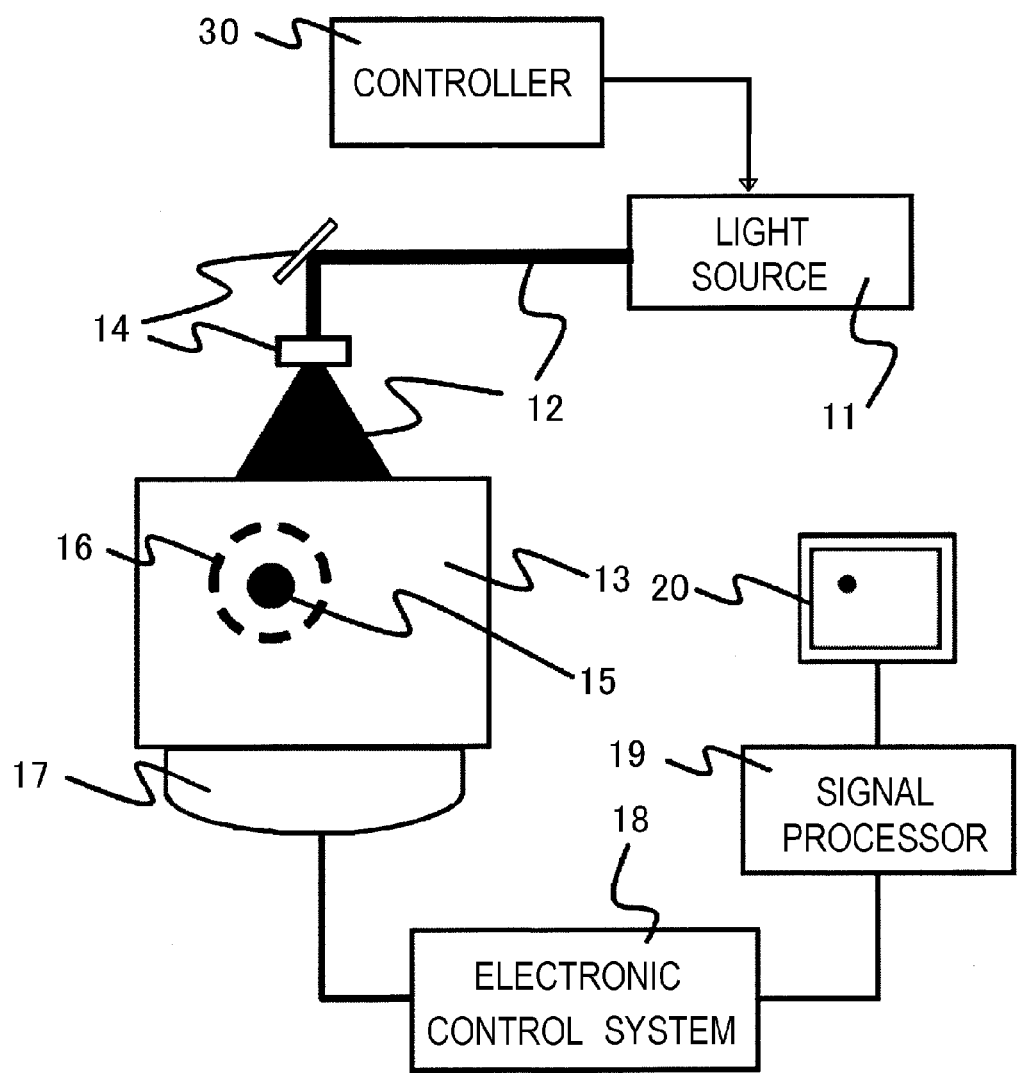
FIG. 1 is a block diagram showing the configuration of an acoustic wave measuring apparatus.

DESCRIPTION OF EMBODIMENTS (Method for Calculating Optical Absorption Coefficient for Single Wavelength)

According to an embodiment of the invention, the wavelength dependency is determined from the acoustic wave obtained by radiating a light having wavelength components in a plurality of wavelength areas. As a prerequisite, a description is given first about a method for calculating an optical absorption coefficient by measuring the acoustic wave using the single-wavelength laser.

The initial sound pressure $P_0$ generated by light radiation is known to be expressed by Equation (1) below.

[Math. 1]

$$P_0 = \Gamma \times \mu_a(\lambda) \times \Phi(\lambda) \tag{1}$$

where $\Gamma$ is the Gruneisen coefficient, $\mu_a(\lambda)$ is the optical absorption coefficient of an absorbing part for the light having the wavelength $\lambda$, $\Phi(\lambda)$ is the amount of an incident light having the wavelength $\lambda$.

Incidentally, the Gruneisen coefficient is a coefficient determined by a substance of the absorbing part and has no dependency on the wavelength of the light. When the light source is the Q-switch YAG laser (wavelength of 1064 nm), therefore, the optical absorption coefficient of the absorbing part for the wavelength of 1064 nm is determined from Equation (2) shown below.

[Math. 2]

$$\mu_a(1064\ nm) = P_0/\Gamma \times \Phi(1064\ nm) \tag{2}$$

Next, a case is described in which the wavelength dependency of the optical absorption coefficient is determined using a variable wavelength laser. As long as the optical absorption coefficient is changed by the wavelength of the light radiated, sound pressures of various values are generated according to the wavelength of the radiated light. Specifically, by changing the wavelength of the radiated light while at the same time measuring the acoustic wave generated for each wavelength, the optical absorption coefficient can be determined for each wavelength.

If four wavelength areas are used, for example, the sound pressure of the acoustic wave generated at the time when the light of each wavelength is absorbed into the absorbing part is expressed by Equations (3) to (6) shown below.

[Math. 3]

$$P_1 = \Gamma \times \mu_a(\lambda_1) \times \Phi(\lambda_1) \tag{3}$$

$$P_2 = \Gamma \times \mu_a(\lambda_2) \times \Phi(\lambda_2) \tag{4}$$

$$P_3 = \Gamma \times \mu_a(\lambda_3) \times \Phi(\lambda_3) \tag{5}$$

$$P_4 = \Gamma \times \mu_a(\lambda_4) \times \Phi(\lambda_4) \tag{6}$$

where $\lambda_1, \lambda_2, \lambda_3$ and $\lambda_4$ are the wavelengths, $P_1, P_2, P_3$ and $P_4$ are the sound pressures.

By solving these equations and determining the optical absorption coefficient for each wavelength, the wavelength dependency of the optical absorption coefficient can be determined.

Equations (3) to (6) can be expressed by a matrix given by Equation (7). The determination of the wavelength dependency of the optical absorption coefficient is equivalent to the inverse matrix calculation of Equation (8) as shown below.

[Math. 4]

$$\begin{pmatrix} P_1 \\ P_2 \\ P_3 \\ P_4 \end{pmatrix} = \Gamma \cdot \begin{pmatrix} \Phi(\lambda_1) & 0 & 0 & 0 \\ 0 & \Phi(\lambda_2) & 0 & 0 \\ 0 & 0 & \Phi(\lambda_3) & 0 \\ 0 & 0 & 0 & \Phi(\lambda_4) \end{pmatrix} \cdot \begin{pmatrix} \mu_a(\lambda_1) \\ \mu_a(\lambda_2) \\ \mu_a(\lambda_3) \\ \mu_a(\lambda_4) \end{pmatrix} \quad (7)$$

$$\begin{pmatrix} \mu_a(\lambda_1) \\ \mu_a(\lambda_2) \\ \mu_a(\lambda_3) \\ \mu_a(\lambda_4) \end{pmatrix} = \frac{1}{\Gamma} \cdot \begin{pmatrix} \Phi(\lambda_1) & 0 & 0 & 0 \\ 0 & \Phi(\lambda_2) & 0 & 0 \\ 0 & 0 & \Phi(\lambda_3) & 0 \\ 0 & 0 & 0 & \Phi(\lambda_4) \end{pmatrix}^{-1} \cdot \begin{pmatrix} P_1 \\ P_2 \\ P_3 \\ P_4 \end{pmatrix} \quad (8)$$

These equations show that if the sound pressure available and the light strength radiated are determined, the wavelength dependency of the optical absorption coefficient can be determined by the simple matrix operation. Also, using the known image reconstruction technique based on the result of the acoustic wave detection, the position of generation and the magnitude of the acoustic wave can be specified so that the physical properties of the absorbing part can be determined.

(Method for Calculating Optical Absorption Coefficient for Plural Wavelength Peaks)

In the method for calculating the wavelength dependency according to the present invention, the optical absorption coefficient is determined by PAT and the wavelength dependency can thus be made clear also for a light source having a multiplicity of bright-line spectra (wavelength peaks) and a light source having the continuous spectrum, by applying the concept for the single wavelength.

In this case, the light irradiating condition described below is set.

TABLE 1

| Light irradiating condition | $\Phi_1$ | $\Phi_2$ | $\Phi_3$ | $\Phi_4$ |
|---|---|---|---|---|
| Sound pressure generated | $P_1$ | $P_2$ | $P_3$ | $P_4$ | where
under each light irradiating condition, the light having four bright-line spectra ($\lambda_1, \lambda_2, \lambda_3, \lambda_4$) is radiated.

The sound pressure in this case is expressed as follows:

[Math. 5]

$$\begin{pmatrix} P_1 \\ P_2 \\ P_3 \\ P_4 \end{pmatrix} = \Gamma \cdot \begin{pmatrix} \Phi_1(\lambda_1) & \Phi_1(\lambda_2) & \Phi_1(\lambda_3) & \Phi_1(\lambda_4) \\ \Phi_2(\lambda_1) & \Phi_2(\lambda_2) & \Phi_2(\lambda_3) & \Phi_2(\lambda_4) \\ \Phi_3(\lambda_1) & \Phi_3(\lambda_2) & \Phi_3(\lambda_3) & \Phi_3(\lambda_4) \\ \Phi_4(\lambda_1) & \Phi_4(\lambda_2) & \Phi_4(\lambda_3) & \Phi_4(\lambda_4) \end{pmatrix} \cdot \begin{pmatrix} \mu_a(\lambda_1) \\ \mu_a(\lambda_2) \\ \mu_a(\lambda_3) \\ \mu_a(\lambda_4) \end{pmatrix} \quad (9)$$

In this case, the light radiation strength is set for each wavelength in such a manner that the determinant of the 4 by 4 matrix in Equation (9) is other than zero. In this way, the wavelength dependency of the optical absorption coefficient can be determined by the inverse matrix operation.

As a result, the optical absorption coefficient described below is obtained.

[Math. 6]

$$\begin{pmatrix} \mu_a(\lambda_1) \\ \mu_a(\lambda_2) \\ \mu_a(\lambda_3) \\ \mu_a(\lambda_4) \end{pmatrix} = \frac{1}{\Gamma} \cdot \begin{pmatrix} \Phi_1(\lambda_1) & \Phi_1(\lambda_2) & \Phi_1(\lambda_3) & \Phi_1(\lambda_4) \\ \Phi_2(\lambda_1) & \Phi_2(\lambda_2) & \Phi_2(\lambda_3) & \Phi_2(\lambda_4) \\ \Phi_3(\lambda_1) & \Phi_3(\lambda_2) & \Phi_3(\lambda_3) & \Phi_3(\lambda_4) \\ \Phi_4(\lambda_1) & \Phi_4(\lambda_2) & \Phi_4(\lambda_3) & \Phi_4(\lambda_4) \end{pmatrix}^{-1} \cdot \begin{pmatrix} P_1 \\ P_2 \\ P_3 \\ P_4 \end{pmatrix} \quad (10)$$

In order to generate each light irradiating condition, the three methods described below are suitably used as a means to control the light radiation strength for each wavelength.

According to a first method, four types of light sources having different radiation spectral characteristics are prepared, and switched at each radiation session.

According to a second method, a light filter for passing or shutting off a specified wavelength is arranged before one light source, and by switching types of the particular light filter, four types of spectra are generated. As this light filter, a notch filter can be suitably used which has such a characteristic that only a specified wavelength is shut off while the light of other wavelengths is transmitted. Specifically, a plurality of notch filters is prepared and arranged on a light path led from the light source to the subject. By pulling off or inserting any of the notch filters mechanically in an appropriate manner during the light radiation, various filter sets can be realized and the light spectrum can be adjusted.

As the light filters used in this case, only the notch filters having the wavelength shutoff characteristic in different wavelength areas may be combined, or the notch filters may be combined, for example, with bandpass filters having different optical characteristics. Alternatively, the spectrum of the light radiated on the subject can be controlled by electrically modulating the wavelength dependency of the transmitted light utilizing the birefringence of the liquid crystal.

A third method uses a micro color filter generally used for the liquid crystal display. Specifically, a plurality of light filters having different characteristics is arranged in juxtaposition, and by stacking an optical on-off switch such as a liquid crystal device at a position corresponding to each filter, the spectrum of the light radiated on the subject is controlled. The light filters, if juxtaposed at excessively long pitches, make it impossible for the light to be radiated under equal conditions on the subject, and therefore, desirably arranged very closely for some types of subjects, or as an alternative, a diffusion plate is arranged after emission from the micro color filter to equalize the light.

Other than the above examples, with the light filters fixedly arranged, the light passed through the filters is turned on and off by a light shutter to control the spectrum of the light radiated on the organism. As an example of this method, a filter can be selected to pass the light path changed by a mirror or the like.

The light with the wavelength spectrum controlled according to the light irradiating condition generated as described above is radiated on the subject. Then, an acoustic wave is generated. This acoustic wave is received at multiple points like in the conventional PAT, and by performing the inverse matrix operation according to the present invention, the wavelength dependency of the optical absorption coefficient can be determined.

Although the light source having four bright-line spectra (wavelength peaks) is described in the above example, a similar concept applies also in the case where a light source of the continuous spectrum is used. Specifically, in the case of the continuous spectrum, as long as the four types of wavelength bands including the three wavelengths involved and another one and the optical strength of each wavelength band are known, the optical absorption coefficient can be determined by Equation (11) shown below.

[Math. 7]

$$\begin{pmatrix} \mu_a(\lambda_1) \\ \mu_a(\lambda_2) \\ \mu_a(\lambda_3) \\ \mu_a(\lambda_{other}) \end{pmatrix} = \frac{1}{\Gamma} \cdot \begin{pmatrix} \Phi_1(\lambda_1) & \Phi_1(\lambda_2) & \Phi_1(\lambda_3) & \Phi_1(\lambda_{other}) \\ \Phi_2(\lambda_1) & \Phi_2(\lambda_2) & \Phi_2(\lambda_3) & \Phi_2(\lambda_{other}) \\ \Phi_3(\lambda_1) & \Phi_3(\lambda_2) & \Phi_3(\lambda_3) & \Phi_3(\lambda_{other}) \\ \Phi_4(\lambda_1) & \Phi_4(\lambda_2) & \Phi_4(\lambda_3) & \Phi_4(\lambda_{other}) \end{pmatrix}^{-1} \cdot \begin{pmatrix} P_1 \\ P_2 \\ P_3 \\ P_4 \end{pmatrix} \quad (11)$$

where $\mu_a(\lambda_{other})$ is a substantially average value of the optical absorption coefficients for the wavelength band other than the wavelengths $\lambda_1$, $\lambda_2$, and $\lambda_3$.

A case involving four types of wavelength is described above, and if the inverse matrix as shown in Equation (10) can be solved, the application is extended to an arbitrary number of determinants.

Also, if required, the laser and a light source other than the laser can be combined as a light source to radiate the light on the subject. Although the safety of laser use is required to be secured in this case, the number of wavelengths required for measurement is probably reduced. As a result, the need of the variable wavelength laser may be eliminated, for example, and the cost of the laser apparatus operation is advantageously reduced partially.

The optical strength used in the calculation described above indicates the strength at a part where the acoustic wave is generated. In the case where a tumor existing in the organism is measured, on the other hand, the light propagates through the organism and generates an acoustic wave by reaching the tumor. The light, while propagating through the organism, is attenuated by diffusion and absorption by the organism. This light attenuation amount depends on the wavelength, and therefore, as long as the wavelength dependency of the optical absorption coefficient and the diffusion coefficient is grasped in advance, the optical strength at the part where the acoustic wave is generated can be determined by calculation. By reflecting this optical strength in Equation (11), the wavelength dependency of the optical absorption coefficient can be determined with higher accuracy.

First Embodiment

FIG. 1 shows the configuration of an acoustic wave measuring apparatus according to the present embodiment. This apparatus includes a light source 11, an optical part 14, a detector 17, an electronic control system 18, a signal processor 19, an image display 20, and a controller 30.

Figure 2:
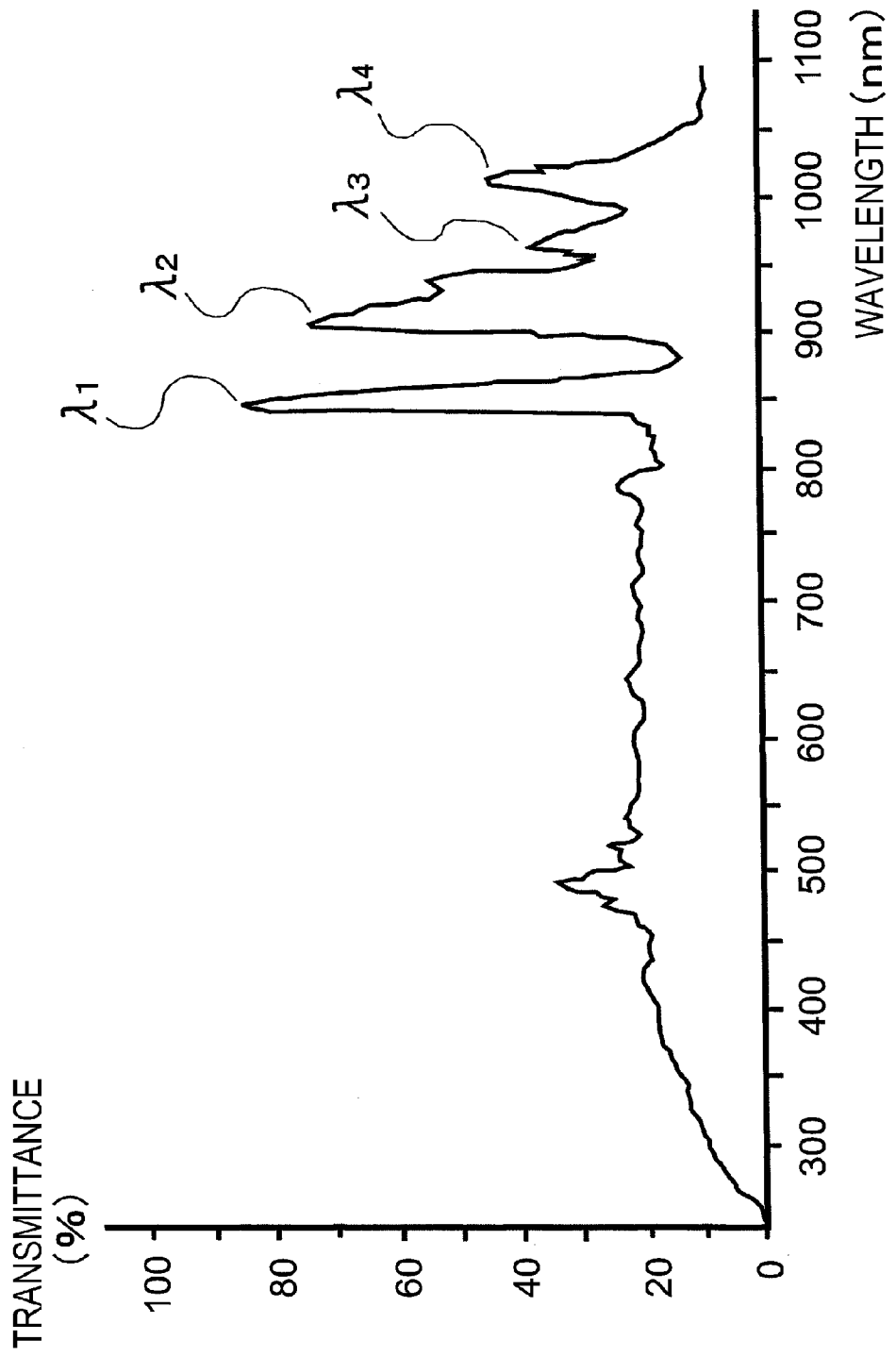
FIG. 2 is a graph showing the wavelength spectral characteristic of a xenon flash lamp.
Figure 4A:
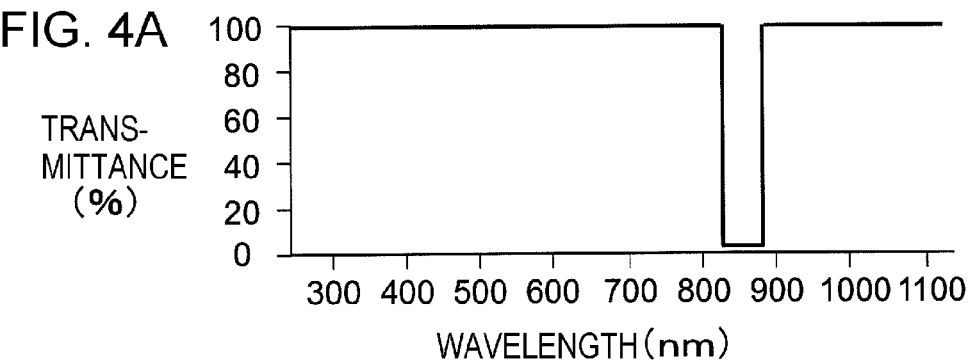
FIG. 4A to FIG. 4D are graphs showing the characteristic of notch filters according to the first embodiment.
Figure 4B:
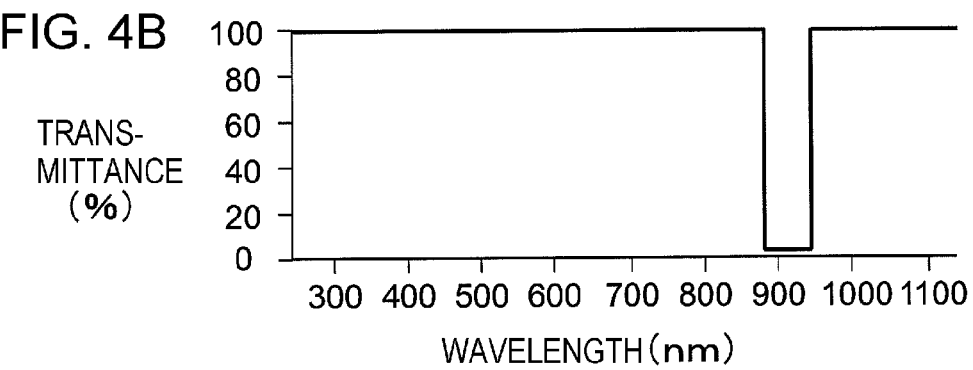
Figure 4C:
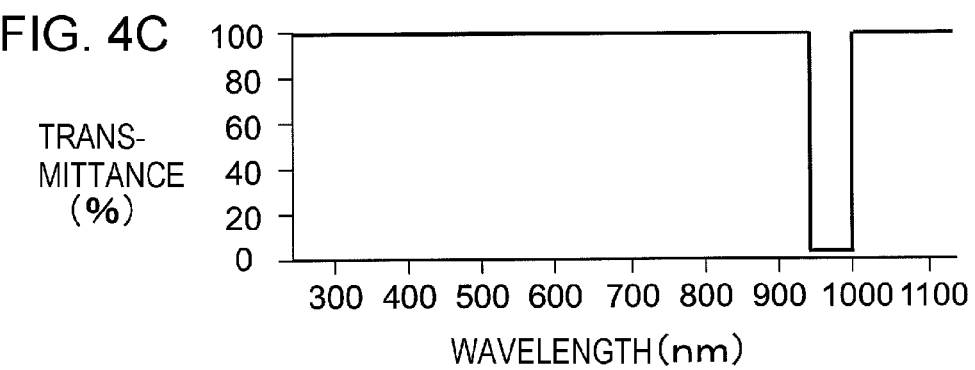
Figure 4D:
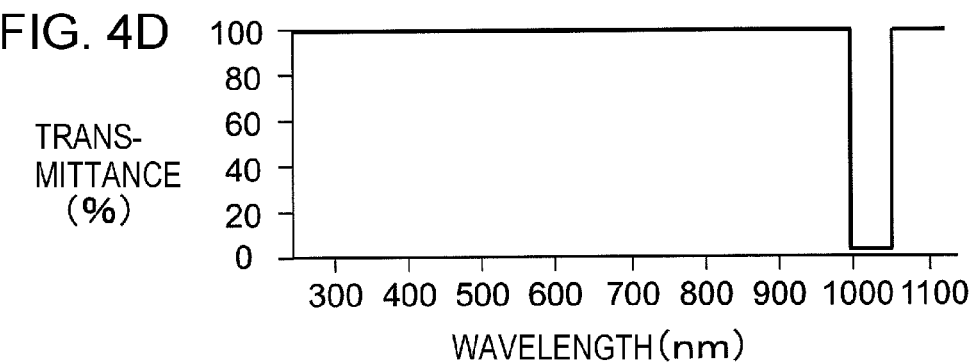

The light source 11 is an optical system configured of a xenon flash lamp and a plurality of light filters. The xenon flash lamp has the bright-line spectrum in the near-infrared area as shown in FIG. 2. The configuration of the light source and a method for controlling the light wavelength structure using the light filters are described in detail later.

The light source 11 radiates the light 12 on the subject 13. Though not shown, the light 12 can also be propagated using an optical waveguide such as an optical fiber. When the optical fiber is used, either the light of each light source can be introduced to the surface of the subject by using the optical fiber, or the light from a plurality of light sources may be led to the optical fiber and radiated on the organism.

The xenon tube used for the light source in this operation desirably has a short light emission time to output the acoustic wave effectively. In a known structure recommended to shorten the light emission time, the glass tube diameter or the electrode interval is reduced. An example of the xenon tube having a short light emission time is the NANOLITE flash lamp of Nobby Tech. Ltd. This product can emit the light with the light emission time of 120 ns and the light emission energy of 150 mJ.

Other than the xenon flash lamp, any light source such as a halogen lamp or an incandescent lamp having the continuous spectrum can also be used. Nevertheless, the light source desirably can realize a short pulse width.

The optical part 14 is a device to radiate the light 12 in the desired shape on the subject 13. An example of the optical part used for this purpose includes a mirror for reflecting the light or a lens for converging or diverging the light or changing the shape of the light.

When the subject is an organism, a lens to enlarge the light to a predetermined areal size is used as the optical part 14 to achieve the optical strength adapted to be radiated on the organism from the viewpoint of MPE. Also, an optical system may be employed which can measure a large area by making an area to be movable in which the subject is irradiated with the laser light. Further, the area in which the subject is irradiated with the light and the detector may be moved in synchronism with each other. As a method for moving the area in which the subject is irradiated with the light, either the movable mirror described above is used or the light source itself may be moved mechanically. By appropriately using the optical part in this way, the direction in which the light proceeds, the part irradiated with the light or the size of the area irradiated can be controlled.

According to the present embodiment, the subject 13 is an organism of a person, and an absorbing part 15 exists in the subject 13. The absorbing part 15 is assumed to have a high optical absorption coefficient as compared with other parts of the subject, and according to the present embodiment, also assumed to be a malignant tumor having many blood vessels containing the oxidized or reduced hemoglobin or newly formed.

Once the radiated light 12 propagates through the subject and reaches the absorbing part 15, an acoustic wave 16 is generated from the absorbing part that has absorbed part of the optical energy.

The detector 17 detects the acoustic wave 16 thus generated and converts the acoustic wave 16 into an electrical signal. Any device that can detect the acoustic wave can be used as detecting elements. A transducer using the piezoelectricity, a transducer using the resonance of light or a transducer using the capacity change is an example. The detector of the acoustic wave measuring apparatus is desirably configured of a plurality of detecting elements arranged two-dimensionally. The use of the two-dimensionally arranged detecting elements makes it possible to detect the acoustic wave at a plurality of points at the same time for a shorter detection time. Further, the effect of the vibration of the subject can be reduced. Also, in order to suppress the reflection of the acoustic wave, it is desirable to use an acoustic impedance matching agent such as gel or water between the detector 17 and the subject.

The electronic control system 18 receives the result of detection by the detector 17, amplifies the electrical signal thus obtained, and converts the electrical signal from an analog signal to a digital signal. The signal processor 19 receives the digital signal from the electronic control system 18, and reconstructs an image by the well-known back projection method. The image reconstructed by the signal processor 19 is displayed on the image display 20. The filtered back projection method normally used for photoacoustic tomography, the Fourier transform method, the spherical radon transform method or the synthetic aperture method can be used as an image reconstruction method. As the result of this reconstruction, the position at which the acoustic wave can be specified and the size of the absorbing part can be determined. The image display 20 may be of any type capable of displaying the image generated by the signal processor. For example, the liquid crystal display is used for this purpose. This image display and other parts make up an acoustic wave imaging apparatus. The controller 30, as described later, controls the wavelength of the radiated light by operating the filter of the optical system of the light source 11.

Incidentally, according to the present embodiment, the light of a plurality of wavelengths is used, and therefore, the distribution of the optical absorption coefficient in the subject is calculated for each wavelength by the system described above. The resultant values thus calculated are compared with the wavelength dependency unique to substances (such as glucose, collagen, oxidized hemoglobin or reduced hemoglobin) making up a tissue of the organism. In this way, the density distribution of the substances making up the organism can be produced as an image.

FIG. 3 shows the optical system around the light source 11. In this optical system, the light flux emitted from the xenon flash lamp 21 is converted by a reflector 22 into light rays 23 proceeding in one direction. Notch filters 25 to 28 have different optical characteristics. Each notch filter, in response to a command from the controller 30, rotates mechanically around the rotational shaft 24 individually and independently to enter or leave the light path.

A method for generating the light irradiating condition by controlling the wavelength spectral characteristics of the radiated light for a combination of these light filters (notch filters) is described below.

The characteristics of the notch filters 25 to 28 are shown in FIGS. 4A to 4D. Each filter has a characteristic to shut off only the wavelength component in a specified wavelength area. As compared with FIG. 2, the wavelength area shut off by each notch filter substantially corresponds to the bright-line spectrum (wavelength peak). The notch filters 25 to 28 are hereinafter sometimes referred to as N1, N2, N3 and N4, respectively. At the time of measurement, N1 to N4 are rendered to enter and leave the light path thereby to control the spectrum of the light radiated on the subject. The condition for the presence or absence of a given notch filter on the light path is set as shown in Table 2 below.

TABLE 2

|  | N1 | N2 | N3 | N4 |
|---|---|---|---|---|
| Condition 1 | Absent | Absent | Absent | Absent |
| Condition 2 | Present | Present | Absent | Absent |
| Condition 3 | Absent | Present | Absent | Present |
| Condition 4 | Absent | Present | Present | Absent |

As described with reference to FIG. 2 above, the xenon flash lamp has four representative bright-line spectra in the near-infrared area. The light emission strength of the wavelength of each of these spectra is set as shown in Table 3 below.

TABLE 3

| Wavelength | $\lambda_1$ | $\lambda_2$ | $\lambda_3$ | $\lambda_4$ |
|---|---|---|---|---|
| Light emission strength | $\Phi(\lambda_1)$ | $\Phi(\lambda_2)$ | $\Phi(\lambda_3)$ | $\Phi(\lambda_4)$ |

In this case, the light amount for each wavelength after passing through the notch filters shown in Table 1 not considering a loss therein is shown in Table 4.

TABLE 4

|  | $\lambda_1$ | $\lambda_2$ | $\lambda_3$ | $\lambda_4$ |
|---|---|---|---|---|
| Condition 1 | $\Phi(\lambda_1)$ | $\Phi(\lambda_2)$ | $\Phi(\lambda_3)$ | $\Phi(\lambda_4)$ |
| Condition 2 | 0 | 0 | $\Phi(\lambda_3)$ | $\Phi(\lambda_4)$ |
| Condition 3 | $\Phi(\lambda_1)$ | 0 | $\Phi(\lambda_3)$ | 0 |
| Condition 4 | $\Phi(\lambda_1)$ | 0 | 0 | $\Phi(\lambda_4)$ |

Under these conditions 1 to 4, the light is radiated on the subject, and the acoustic wave strengths $P_1$ to $P_4$ are determined for the respective conditions. Thus, a determinant is generated as shown in Equation (12). The determinant of the 4 by 4 matrix on the right side of this equation is not zero, and therefore, the inverse matrix can be determined as shown in Equation (13). Thus, the optical absorption coefficient can be determined.

[Math. 8]

$$\begin{pmatrix} P_1 \\ P_2 \\ P_3 \\ P_4 \end{pmatrix} = \Gamma \cdot \begin{pmatrix} \Phi(\lambda_1) & \Phi(\lambda_2) & \Phi(\lambda_3) & \Phi(\lambda_4) \\ 0 & 0 & \Phi(\lambda_3) & \Phi(\lambda_4) \\ \Phi(\lambda_1) & 0 & \Phi(\lambda_3) & 0 \\ \Phi(\lambda_1) & 0 & 0 & \Phi(\lambda_4) \end{pmatrix} \cdot \begin{pmatrix} \mu_a(\lambda_1) \\ \mu_a(\lambda_2) \\ \mu_a(\lambda_3) \\ \mu_a(\lambda_4) \end{pmatrix} \quad (12)$$

$$\begin{pmatrix} \mu_a(\lambda_1) \\ \mu_a(\lambda_2) \\ \mu_a(\lambda_3) \\ \mu_a(\lambda_4) \end{pmatrix} = \frac{1}{\Gamma} \cdot \begin{pmatrix} \Phi(\lambda_1) & \Phi(\lambda_2) & \Phi(\lambda_3) & \Phi(\lambda_4) \\ 0 & 0 & \Phi(\lambda_3) & \Phi(\lambda_4) \\ \Phi(\lambda_1) & 0 & \Phi(\lambda_3) & 0 \\ \Phi(\lambda_1) & 0 & 0 & \Phi(\lambda_4) \end{pmatrix}^{-1} \cdot \begin{pmatrix} P_1 \\ P_2 \\ P_3 \\ P_4 \end{pmatrix} \quad (13)$$

By operating the inverse matrix on the right side, the wavelength dependency of the optical absorption coefficient can be determined.

As described above, according to the present embodiment, the spectrum of the radiated light can be adjusted and the acoustic wave can be measured using the xenon flash lamp and the notch filters without any expensive laser light source as an apparatus. As a result, the characteristic of the subject, or especially, that of the absorbing part can be grasped with a simple matrix operation.

Incidentally, the essence of the present invention is to determine the wavelength dependency of the optical absorption coefficient by controlling the wavelength spectral characteristic of the light radiated on the subject. In view of this, the filter system described above may be replaced with a system in which a plurality of light sources having different wavelength spectral characteristics is used by switching.

Second Embodiment

Figure 6:
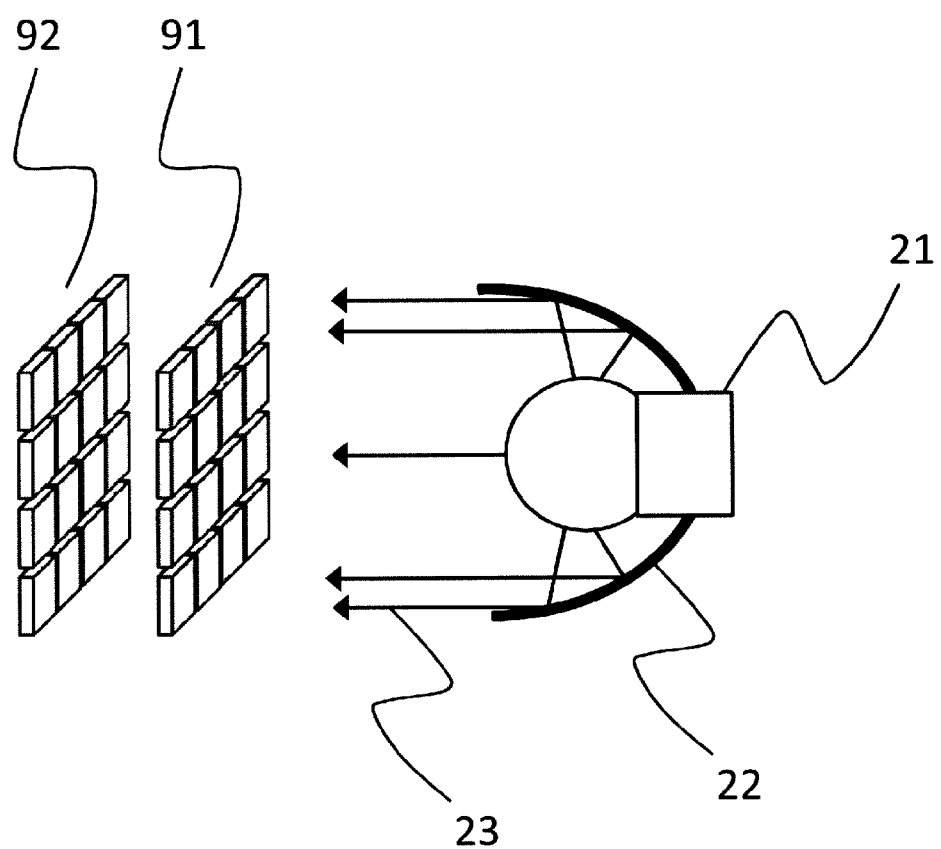
FIG. 6 is a diagram showing a light source according to the second embodiment.

The present embodiment is described with reference to a case in which the micro color filter system is used as a method for controlling the spectrum of the radiated light. FIG. 5 shows the manner in which the micro color filter is configured of a plurality of closely juxtaposing bandpass filters B1 to B4. Reference characters B1 to B4 designate the bandpass filters corresponding to the four wavelength peaks, respectively, of the xenon flash lamp. The bandpass filters B1 to B4 transmit only the light in the wavelength area containing the corresponding peaks, respectively. Also, FIG. 6 shows the manner in which the micro color filter shown in FIG. 5 is used for the optical system. In FIG. 6, the light source is similar to that of the embodiment described above, and the second embodiment is different from the first embodiment in that the former has a light shutter 91 and a micro color filter 92.

The pixels of the micro color filter 91 are arranged at the same pitch as the pitch at which the bandpass filters are laid closely to each other as shown in FIG. 5. According to a decision of the controller, the on-off operation of each bandpass filter can be controlled individually and independently. By doing so, the spectrum of the radiated light is controlled and the light irradiating condition shown in Table 4 can be realized.

The transmission-type liquid crystal panel in a matrix-like shape can be used as the light shutter 91. The liquid crystal panel of active matrix type which can produce a high contrast is preferable. From the viewpoint of the mechanical aperture, however, the simple matrix is more advantageous. Therefore, any of these two types of liquid crystal panels can be used as a preferable one in each particular application.

As described above, the spectrum of the light radiated on the subject can be controlled properly by controlling the light from the light source using the light shutter and the bandpass filter. The acoustic wave generated from the subject by the radiated light is measured, and the matrix operation performed using the sound pressure and the optical strength. In this way, the optical absorption coefficient can be determined. As a result, the characteristic of the absorbing part can be grasped by measuring the acoustic wave without the laser apparatus.

Incidentally, the light filter used in the present embodiment is not limited to the bandpass filter. Any arbitrary filters or any combination thereof can be used which can control the shut-off and transmission for each wavelength area in such a manner as to satisfy the various light irradiating conditions. Also, the light irradiating conditions are not limited to those shown in Table 4 and any light irradiating conditions according to which the inverse matrix can be operated by generating a determinant are applicable.

Third Embodiment

Figure 7:
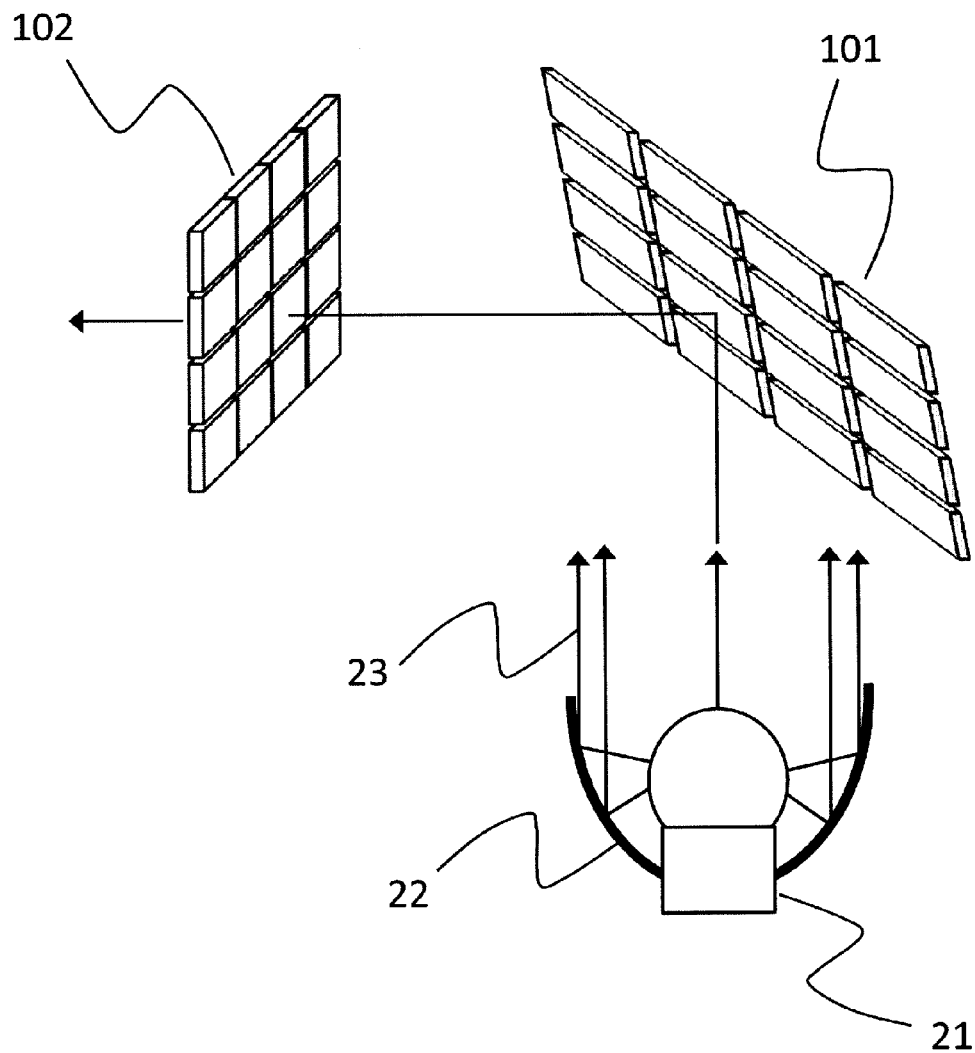
FIG. 7 is a diagram showing a light source according to a third embodiment.

In the present embodiment, a case is described in which a device of reflection type is used in a method for controlling the spectrum of the radiated light. FIG. 7 shows the configuration of the optical system according to the present embodiment. A light source portion and a micro color filter 102 have the same configuration as those in the embodiments described above.

A reflection-type device 101 reflects the light from the light source and guides it to the micro color filter. In the process, reflection or non-reflection of the light can be controlled in accordance with the pixel pitch of the bandpass filter. As a result, the spectrum of the radiated light can be controlled.

Like in the second embodiment, the liquid crystal panel can be used as the reflection-type device. From the viewpoint of the reflectivity, however, it is not preferable not to use a polarization plate. Instead, a digital mirror device (DMD) is a preferable choice. A multiplicity of micro mirrors is arranged in matrix on the surface of a DMD and an on-off operation of each micro mirror can be controlled individually and independently. According to a decision of a controller, the radiation spectrum is controlled and the light irradiating condition can be realized as shown in Table 4.

As described above, the light radiated from the light source is controlled using the reflection-type device and the micro color filter (bandpass filter). In this way, the spectrum of the light radiated on the subject can be properly controlled. As a result, the acoustic wave can be measured and the characteristics of an absorbing part can be grasped without using a laser apparatus.

Incidentally, the light filter used in the present embodiment is not limited to the bandpass filter. Any of filters or any combination thereof can be used which can control the shut-off and transmission for each wavelength area in such a manner as to satisfy the various light irradiating conditions. Also, the light irradiating condition is not limited to those shown in Table 4 and any light irradiating condition according to which the inverse matrix can be operated by generating a determinant is applicable.

Fourth Embodiment

Figure 8:
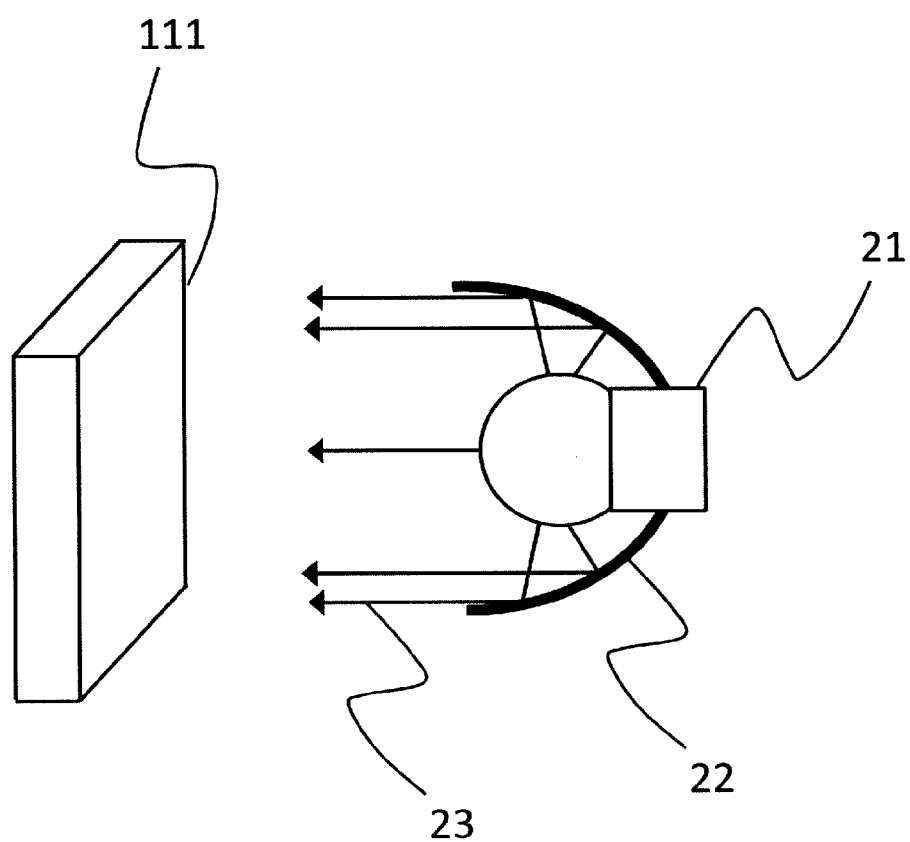
FIG. 8 is a diagram showing a light source according to a fourth embodiment.

In the present embodiment, a method using a liquid crystal panel as a variable wavelength filter is described. FIG. 8 shows a configuration of an optical system according to the present embodiment. The light source portion has the same configuration as that of the embodiments described above. A variable wavelength filter 111 is configured of two polarization plates as a crossed nicol, between which a liquid cell with a transparent electrode is arranged. The transmittance T in this case is given by the equation shown below.

[Math. 9]

$$T\% \propto \sin^2\left(\frac{\pi \cdot \Delta n_{\mathit{eff}} \cdot d}{\lambda}\right) \quad (14)$$

where
$\Delta n_{\mathit{eff}}$ is a refractive index of an effective liquid crystal layer,
d is the thickness of liquid crystal cell,
$\lambda$ is a wavelength.

Incidentally, the refractive index of the liquid crystal layer can be changed within a predetermined range by modulating the voltage value applied to the transparent electrode.

As understood from this equation, the transmittance depends on the wavelength and can be changed by changing the applied voltage. By changing the voltage application condition and thus controlling the transmittance, therefore, the spectrum of the radiated light can be controlled like in the above embodiments.

When N cells of crossed nicols and M cells of parallel nicols are stacked in this variable wavelength filter, the transmittance is equal to the product of all the panels. In this state, the transmittance T can be expressed by the equation below. By stacking cells in this way, the transmittance can be controlled more freely.

[Math. 10]

$$T\% \propto \prod_{i=1}^{N}\sin^2\left(\frac{\pi \cdot \Delta n_{\mathit{eff\_i}} \cdot d_i}{\lambda}\right) \cdot \prod_{j=1}^{M}\cos^2\left(\frac{\pi \cdot \Delta n_{\mathit{eff\_j}} \cdot d_j}{\lambda}\right) \quad (15)$$

As described above, the light radiated from the light source is controlled using the reflection-type device and the micro color filter (notch filter). In this way, the spectrum of the light radiated on the subject can be properly controlled. As a result, the acoustic wave can be measured and the characteristics of the absorbing part can be grasped without using the laser apparatus.

Fifth Embodiment

In the present embodiment, a system configuration is employed in which the apparatus configuration described in the foregoing embodiments is combined with the alexandrite laser capable of generating the laser light having the wavelength of 755 nm. In the present embodiment, a notch filter corresponding to the notch filter N4 of the first embodiment in always in operation. In this state, four conditions are set for light radiation with the optical strength for each wavelength shown in Table 5.

TABLE 5

|  | $\lambda_1$ | $\lambda_2$ | $\lambda_3$ | 755 nm | $\lambda_4$ |
| --- | --- | --- | --- | --- | --- |
| Condition 1 | $\Phi(\lambda_1)$ | $\Phi(\lambda_2)$ | $\Phi(\lambda_3)$ | $\Phi(755\ nm)$ | 0 |
| Condition 2 | 0 | 0 | $\Phi(\lambda_3)$ | $\Phi(755\ nm)$ | 0 |
| Condition 3 | $\Phi(\lambda_1)$ | 0 | $\Phi(\lambda_3)$ | 0 | 0 |
| Condition 4 | $\Phi(\lambda_1)$ | 0 | 0 | $\Phi(755\ nm)$ | 0 |

The fourth wavelength peak is not considered, and the calculation is made with the remaining four wavelengths. Then, the determinant described below can be set.

[Math. 11]

$$\begin{pmatrix} \mu_a(\lambda_1) \\ \mu_a(\lambda_2) \\ \mu_a(\lambda_3) \\ \mu_a(755\ nm) \end{pmatrix} = \frac{1}{\Gamma} \cdot \begin{pmatrix} \Phi(\lambda_1) & \Phi(\lambda_2) & \Phi(\lambda_3) & \Phi(755\ nm) \\ 0 & 0 & \Phi(\lambda_3) & \Phi(755\ nm) \\ \Phi(\lambda_1) & 0 & \Phi(\lambda_3) & 0 \\ \Phi(\lambda_1) & 0 & 0 & \Phi(755\ nm) \end{pmatrix}^{-1} \cdot \begin{pmatrix} P_1 \\ P_2 \\ P_3 \\ P_4 \end{pmatrix} \quad (16)$$

By solving this equation, an optical absorption coefficient for a wavelength of 755 nm can be determined. In this way, a measurement accuracy of the optical absorption coefficient can be improved at about 800 nm where relative magnitudes of the optical absorption coefficients of the oxidized hemoglobin and the reduced hemoglobin are reversed. As a result, the absorbing part can be easily grasped for an improved diagnosis accuracy.

The present embodiment uses the laser and requires the security equipment. The absence of the variable wavelength laser, however, can realize a relatively inexpensive apparatus.

The technique described in the embodiments above can realize a simple, highly safe acoustic wave measuring apparatus. Specifically, the absence of the high-output variable wavelength pulse laser simplifies the optical system and can realize an inexpensive, reliable apparatus. Also, since the accessorial equipment for safety against laser is not required, the apparatus becomes handy.

Also, the employment of the apparatus configuration of hand-held type is facilitated. In the apparatus of hand-held type, the operator can detect the state in the organism by applying an ultrasonic probe to an affected part freely in the same manner as if the ordinary ultrasonic echo diagnosis apparatus is handled. When the laser is used, the laser light is required to be radiated from the forward end of the photoacoustic probe of hand-held type, which in turn requires the strict management to prevent the strong laser light from entering the eyes directly or indirectly. According to the first to fourth embodiments, on the other hand, no laser is used. Even if the light enters the eye directly or indirectly, therefore, the retina is not substantially affected though somewhat dazzling. As a result, a highly safe hand-held apparatus can be realized. Also, in the first to forth embodiments of the invention, no laser is used, so that the eyes of a fetus, if observed in the same manner as in the conventional ultrasonic diagnosis apparatus, are not adversely affected.

Further, by processing the signal of the acoustic wave, the image is reconstructed and the physical properties of the tissue can be grasped. At the same time, not only the internal state of the organism but also the characteristic of the surface of the organism can be easily grasped. The ratio of collagen existing in the coria and the percent of the local body fat, for example, can be measured, without laser management, by the safe and simple apparatus according to the invention. Furthermore, the present invention can be implemented also as a method for controlling the acoustic wave measuring apparatus described above.

Incidentally, the subject may include the breast, fingers, hands and legs of a human and other animals as an object of diagnosing a malignant tumor or a blood disease or observing the progress of a chemical treatment. Also, the constant medium introduced from outside of the organism can be used as an absorbing part.

The apparatus according to the present invention is not only used for the organism but also can be realized as a substance measuring apparatus for detection of gas or foreign matter or surface diagnosis more easily than with the laser.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-240299, filed on Oct. 19, 2009, which is hereby incorporated by reference herein its entirety.

The invention claimed is:

1. An acoustic wave measuring apparatus comprising:
a light source that radiates light having a wavelength component in a plurality of wavelength areas;
a plurality of light filters that shut off the light in a specified one of the plurality of wavelength areas respectively;
a plurality of reflection-type devices that reflects light radiated from said light source to said plurality of light filters;
a detector that detects an acoustic wave generated upon light radiation on the subject;
a controller that changes a combination of said light filters and thus generates a plurality of light irradiating conditions having different combinations of the wavelength components contained in the light radiated on the subject; and a signal processor that calculates an optical absorption coefficient of the subject for the light in each of the plurality of wavelength areas, based on a pressure of the acoustic wave detected under each of the plurality of light irradiating conditions and a strength of the radiated light for each of the plurality of the light irradiating conditions, wherein said plurality of light filters are arranged in a matrix-like shape, wherein said plurality of reflection-type devices are arranged in a matrix-like shape corresponding to said plurality of light filters and individually switches whether the light radiated from said light source is reflected to each of said plurality of light filters, and wherein said controller generates the plurality of light irradiating conditions by controlling whether each of said plurality of reflection-type devices reflects the light radiated from said light source to each of said plurality of light filters.

2. The acoustic wave measuring apparatus according to claim 1, wherein said light source is a xenon flash lamp.

3. The acoustic wave measuring apparatus according to claim 2,
wherein each of said light filters is a notch filter that shuts off the light in a respective one of wavelength peaks of said xenon flash lamp.

4. The acoustic wave measuring apparatus according to claim 1,
wherein said detector includes a plurality of detecting elements, and
said signal processor obtains a density distribution of substances from a calculated optical absorption coefficient and causes an image display to display an image of the density distribution of the substances.

5. The acoustic wave measuring apparatus according to claim 4, further comprising said image display.

6. The acoustic wave measuring apparatus according to claim 1, wherein each of said plurality of light filters shuts off or transmits the light in a respective one of wavelength peaks of said light source.

7. The acoustic wave measuring apparatus according to claim 1, wherein said plurality of reflection-type devices is a digital mirror device.

8. An acoustic wave measuring apparatus comprising:
a light source that radiates light having wavelength components in a plurality of wavelength areas;
a plurality of light filters each of which shuts off the light in a specified one of the plurality of wavelength areas respectively;
a plurality of light shutters arranged on a light path from said light source to said plurality of light filters;
a detector that detects an acoustic wave generated upon light radiation of a subject;
a controller that changes a combination of said plurality of light filters and thus generates a plurality of light irradiating conditions having different combinations of the wavelength components contained in the light with which the subject is irradiated; and
a signal processor that calculates an optical absorption coefficient of the subject for the light in each of the plurality of wavelength areas, based on a pressure of the acoustic wave detected under each of the plurality of light irradiating conditions and a strength of the radiated light for each of the plurality of light irradiating conditions, wherein said plurality of light filters are arranged in a matrix-like shape, wherein said plurality of light shutters are arranged in a matrix-like shape corresponding to said plurality of light filters and individually switch whether the light radiated from said light source is shut off, and wherein said controller generates the plurality of light irradiating conditions by controlling whether each of said plurality of light shutters shuts off the light radiated from said light source.

9. The acoustic wave measuring apparatus according to claim 8, wherein said light source is a xenon flash lamp.

10. The acoustic wave measuring apparatus according to claim 9, wherein each of said plurality of said light filters is a notch filter that shuts off the light in a respective one of wavelength peaks of said xenon flash lamp.

11. The acoustic wave measuring apparatus according to claim 8,
wherein said detector includes a plurality of detecting elements, and
wherein said signal processor obtains a density distribution of substances from a calculated optical absorption coefficient and causes an image display to display an image of the density distribution of the substances.

12. The acoustic wave measuring apparatus according to claim 11, further comprising said image display.

13. The acoustic wave measuring apparatus according to claim 8, wherein each of said plurality of light filters shuts off or transmits the light in a respective one of wavelength peaks of said light source.

14. The acoustic wave measuring apparatus according to claim 8, wherein said plurality of light shutters is a liquid crystal device.

15. An acoustic wave measuring apparatus comprising:
a light source that radiates light having wavelength components in a plurality of wavelength areas;
a plurality of light filters each of which shuts off the light in a specified one of the plurality of wavelength areas respectively;
a plurality of optical elements arranged on a light path from said light source to a medium;
a detector that detects an acoustic wave generated upon light radiation of a subject;
a controller that changes a combination of said plurality of light filters and thus generates a plurality of light irradiating conditions having different combinations of the wavelength components contained in the light with which the subject is irradiated; and
a signal processor that calculates an optical absorption coefficient of the subject for the light in each of the plurality of wavelength areas, based on a pressure of the acoustic wave detected under each of the plurality of light irradiating conditions and a strength of the radiated light for each of the plurality of light irradiating conditions, wherein said plurality of light filters are arranged in a matrix-like shape, wherein said plurality of optical elements are arranged in a matrix-like shape corresponding to said plurality of light filters and individually switches whether the light radiated from said light source is led to the medium via a respective one of said plurality of light filters, and wherein said controller generates the plurality of light irradiating conditions by controlling whether each of said plurality of optical elements leads the light radiated from said light source to the medium via said respective ones of said plurality of light filters.

* * * * *